US012472137B2

(12) United States Patent
Yuki

(10) Patent No.: US 12,472,137 B2
(45) Date of Patent: Nov. 18, 2025

(54) AEROSOL-TYPE HAIR CLEANSING AGENT

(71) Applicant: KAO CORPORATION, Tokyo (JP)

(72) Inventor: Katsuyuki Yuki, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 430 days.

(21) Appl. No.: 18/000,042

(22) PCT Filed: Apr. 5, 2021

(86) PCT No.: PCT/JP2021/014429
§ 371 (c)(1),
(2) Date: Nov. 28, 2022

(87) PCT Pub. No.: WO2021/241004
PCT Pub. Date: Dec. 2, 2021

(65) Prior Publication Data

US 2023/0201100 A1 Jun. 29, 2023

(30) Foreign Application Priority Data

May 29, 2020 (JP) ................................ 2020-094429

(51) Int. Cl.
*A61K 8/02* (2006.01)
*A61K 8/04* (2006.01)
*A61K 8/19* (2006.01)
*A61K 8/46* (2006.01)
*A61K 8/86* (2006.01)
*A61Q 5/02* (2006.01)

(52) U.S. Cl.
CPC ................ *A61K 8/86* (2013.01); *A61K 8/046* (2013.01); *A61Q 5/02* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 6,627,565 | B1 | 9/2003 | Steer |
| 2013/0102513 | A1 | 4/2013 | Terada |
| 2014/0246515 | A1 | 9/2014 | Nakajima |
| 2018/0110702 | A1 | 4/2018 | Constantine et al. |
| 2023/0190591 | A1 | 6/2023 | Mieno et al. |

FOREIGN PATENT DOCUMENTS

| | | | | |
|---|---|---|---|---|
| CN | 103930513 A | | 7/2014 | |
| CN | 109602659 A | | 4/2019 | |
| EP | 1 792 600 A1 | | 6/2007 | |
| JP | 2001-507031 A | | 5/2001 | |
| JP | 2003-501452 A | | 1/2003 | |
| JP | 2012-1512 A | | 1/2012 | |
| JP | 2012-136485 A | | 7/2012 | |
| JP | 2015 098463 | * | 5/2015 | ............... A61K 8/55 |
| JP | 2015-98463 A | | 5/2015 | |
| JP | 2015-101545 A | | 6/2015 | |
| JP | 2016-183134 A | | 10/2016 | |
| JP | 2017 137254 | * | 8/2017 | ............... A61K 8/81 |
| JP | 2017-137254 A | | 8/2017 | |
| JP | 2017-155011 A | | 9/2017 | |
| JP | 2018-95616 A | | 6/2018 | |
| JP | 6639176 B2 | | 2/2020 | |
| JP | 2021-187836 A | | 12/2021 | |
| TW | 201701859 A | | 1/2017 | |
| WO | WO-88/27935 A1 | | 7/1998 | |
| WO | WO 2013/172475 A2 | | 11/2013 | |

OTHER PUBLICATIONS

International Search Report mailed on May 18, 2021 in PCT/JP2021/014429 filed on Apr. 5, 2021 (2 pages).
Extended European Search Report issued Apr. 23, 2025 in European Patent Application No. 21812381.8, 6 pages.

* cited by examiner

*Primary Examiner* — Brian Gulledge
(74) *Attorney, Agent, or Firm* — Oblon, McClelland, Maier & Neustadt, L.L.P.

(57) ABSTRACT

An aerosol hair cleansing agent comprising a hair cleansing agent stock solution containing a surfactant (A) containing an anionic surfactant (A1) and two or more nonionic polymers (B) having weight average molecular weights different from each other, and a propellant (C) containing carbon dioxide. The component (B) contains a nonionic polymer (B1) having a weight average molecular weight of 1,000,000 or more and 5,000,000 or less and contains a nonionic polymer (B2) having a weight average molecular weight of 10,000 or more and 200,000 or less.

10 Claims, No Drawings

AEROSOL-TYPE HAIR CLEANSING AGENT

CROSS REFERENCE TO RELATED APPLICATIONS

This application is a National Stage entry under 35 U.S.C. § 371 of PCT/JP2021/014429, filed on Apr. 5, 2021, and claims priority to Japanese Patent Application No. 2020-094429, filed on May 29, 2020. The entire contents of both are incorporated herein by reference.

FIELD OF THE INVENTION

The present invention relates to an aerosol type hair cleansing agent.

BACKGROUND OF THE INVENTION

Aerosol type cosmetic preparations have an advantage that the cosmetic preparation as a hair cleansing agent stock solution can be easily coated and spread on the skin or the hair since the cosmetic preparation can be used by discharging in the form of foam type.

Aerosol type cosmetic preparations have been demanded to have good quality of foam immediately after discharging (foamability), and good storage stability, and the like.

It has been known that carbon dioxide gas is used as a propellant of the aerosol type cosmetic preparations. The aerosol type cosmetic preparation using carbon dioxide as a propellant can discharge foam with a creamy and elastic texture, and furthermore the foam is retained for a long period of time without immediate loss thereof. Moreover, by entraining carbon dioxide gas in the discharged foam, the carbon dioxide gas is expected to have an effect of functioning as a cosmetic care ingredient, such as an aging care ingredient, in application to the skin or the hair.

As aerosol type cosmetics using carbon dioxide gas as a propellant, for example, Patent Literature 1 (JP 2015-098463 A) describes that a foamable coating composition containing an aqueous stock solution containing a high polymerization degree polyethylene glycol, a polyhydric alcohol, an ionic surfactant, and water, and a propellant containing carbon dioxide is excellent in stability of the contents without deposition of the ionic surfactant and is excellent in foamability, extensibility, and adherability to the skin of the discharged matter. There is also described that the foamable coating composition is used as a product used by coating and spreading on the head hair, such as a treatment agent, a hair pack, and a shampoo.

SUMMARY OF THE INVENTION

The present invention relates to an aerosol type hair cleansing agent containing a hair cleansing agent stock solution containing a surfactant (A) containing an anionic surfactant (A1) and two or more kinds of nonionic polymers (B) having weight average molecular weights different from each other, and a propellant (C) containing carbon dioxide.

DETAILED DESCRIPTION OF THE INVENTION

Aerosol Type Hair Cleansing Agent

The aerosol type hair cleansing agent of the present invention (which may be hereinafter referred simply to as a "hair cleansing agent of the present invention") contains a hair cleansing agent stock solution containing a surfactant (A) containing an anionic surfactant (A1) and two or more kinds of nonionic polymers (B) having weight average molecular weights different from each other, and a propellant (C) containing carbon dioxide.

In the present invention, the expression "to have a component X" and "to contain a component X" also mean "to be formed by mixing a component X".

In the present invention, the storage stability at a temperature of 5° C. or less is used as an index of the "storage stability under a low temperature environment". In the following description, the "storage stability under a low temperature environment" may be referred simply to as "low temperature stability".

A polymer having a high molecular weight, such as a high polymerization-degree polyethylene glycol, mixed in an aerosol composition results in a tendency of deteriorating any one or both of the quality of foam immediately after discharging and the storage stability, and in particular, there is room for improvement in storage stability of the composition under a low temperature environment.

In the case where the aerosol type cosmetic hair preparation is a hair cleansing agent, furthermore, the foaming in cleansing the hair (which may be hereinafter referred to as the "refoamability"), the cleansability due to good slippiness of foam, and the good feeling of the hair after cleansing are also demanded in addition to the quality of foam immediately after discharging and the storage stability. However, PTL 1 does not investigate these effects, and there is room for improvement therefor.

A problem to be solved by the present invention is to provide an aerosol type hair cleansing agent that is excellent in storage stability under a low temperature environment and quality of foam immediately after discharging, and is also good in refoamability in cleansing the hair, slippiness of foam, and good feeling of the hair after cleansing.

The present inventors have found that the problem can be solved by an aerosol type hair cleansing agent that contains a hair cleansing agent stock solution containing a surfactant containing an anionic surfactant and prescribed two or more kinds of nonionic polymers, and a propellant containing carbon dioxide.

According to the present invention, an aerosol type hair cleansing agent that is excellent in storage stability under a low temperature environment and quality of foam immediately after discharging, and is also good in refoamability in cleansing the hair, slippiness of foam, and good feeling of the hair after cleansing can be provided.

The mechanism that the hair cleansing agent of the present invention can exhibit the effects of the present invention due to the aforementioned configuration thereof is still not clear, but can be estimated as follows.

The hair cleansing agent stock solution as an aerosol stock solution used in the aerosol type hair cleansing agent of the present invention contains a surfactant (A) containing an anionic surfactant (A1) and two or more kinds of nonionic polymers (B) having weight average molecular weights different from each other, and contains carbon dioxide as a propellant (C).

The surfactant as the component (A) is used for imparting the dischargeability of foam through aerosol effect and the target capability of the hair cleansing agent. The surfactant (A) contains the anionic surfactant (A1), and thereby the cleansability can be imparted.

The nonionic polymers as the component (B) mixed in the hair cleansing agent stock solution enable the entrainment of the gas of the propellant (C) in the discharged foam, and thus improves the quality of foam. It is considered that the use of carbon dioxide as the propellant can discharge fine dense foam, which improves the quality of foam immediately after discharging and the refoamability in cleansing the hair.

As a result of the investigation by the present inventors, however, it has been found that the effects to be obtained vary depending on the molecular weight of the nonionic polymer.

More specifically, for example, the use of a nonionic polymer having a relatively high weight average molecular weight (for example, 1,000,000 or more) has a high effect of entraining the gas of the propellant (C) in the discharged foam, providing good slippiness of foam in cleansing the hair. However, it has been found that there is a tendency that any of the quality of foam immediately after discharging, the storage stability at a low temperature, and the feeling of the hair after cleansing is deteriorated. On the other hand, there is a tendency that the use of a nonionic polymer having a relatively low weight average molecular weight (for example, 200,000 or less) improves the storage stability at a low temperature and the feeling of the hair after cleansing, but deteriorates the slippiness of foam in cleansing the hair.

It is considered that in the hair cleansing agent of the present invention, two or more kinds of nonionic polymers having weight average molecular weights different from each other are used as the component (B) in the hair cleansing agent stock solution, and simultaneously a propellant containing carbon dioxide is used as the component (C), thereby resulting in a hair cleansing agent that achieves all the storage stability under a low temperature environment, the quality of foam immediately after discharging, the refoamability in cleansing the hair, the slippiness of foam, and the feeling of the hair after cleansing.

Component (A): Surfactant

The hair cleansing agent stock solution constituting the hair cleansing agent of the present invention contains a surfactant as a component (A). The component (A) is used for imparting the dischargeability of foam through aerosol effect and the target capability of the hair cleansing agent.

In the hair cleansing agent stock solution in the present invention, the component (A) contains an anionic surfactant (A1) from the standpoint of imparting the cleansability.

Anionic Surfactant (A1)

Examples of the anionic surfactant (A1) include an alkylbenzene sulfonate salt, an alkyl or alkenyl ether sulfate salt, an alkyl or alkenyl sulfate salt, an alkyl sulfonate salt, a saturated or unsaturated fatty acid salt, an alkyl or alkenyl ether carboxylate salt, an α-sulfo fatty acid salt, an N-acylamino acid salt, a phosphoric acid mono- or diester salt, and a sulfosuccinic acid ester salt, and one kind or two or more kinds thereof may be used.

The hydrocarbon group, such as the alkyl group and the alkenyl group, and the constitutional fatty acid of the anionic surfactant preferably has 8 or more and 22 or less carbon atoms, more preferably 8 or more and 18 or less carbon atoms, and further preferably 10 or more and 18 or less carbon atoms.

Examples of the counter ion of the anionic group of the anionic surfactant include an alkali metal ion, such as sodium ion and a potassium ion; an alkaline earth metal ion, such as a calcium ion and magnesium ion; an ammonium ion; and an alkanolammonium having 1 to 3 alkanol group having 2 or 3 carbon atoms (such as monoethanolammonium, diethanolammonium, triethanolammonium, and triisopropanolammonium).

Among the above, the anionic surfactant is preferably one or more kind selected from the group consisting of an alkyl sulfate salt, an alkyl ether sulfate salt, an alkyl ether carboxylate salt, and an N-acylamino acid salt from the standpoint of the use as a hair cleansing agent. Examples of the alkyl sulfate salt include sodium lauryl sulfate. Examples of the alkyl ether sulfate salt include a polyoxyethylene alkyl ether sulfate salt, such as sodium laureth sulfate and ammonium laureth sulfate, and examples of the alkyl ether carboxylate salt include a polyoxyethylene alkyl ether acetate, such as sodium laureth acetate. Examples of the N-acylamino acid salt include an N-acylglutamate, such as sodium cocoyl glutamate.

The anionic surfactant (A1) is more preferably one or more kind selected from the group consisting of an alkyl ether sulfate salt and an N-acylamino acid salt, and further preferably one or more kind selected from the group consisting of sodium laureth sulfate, ammonium laureth sulfate, and sodium cocoyl glutamate.

The content of the anionic surfactant (A1) in the component (A) is preferably 50% by mass or more, more preferably 70% by mass or more, further preferably 80% by mass or more, and still further preferably 90% by mass or more, and may be 100% by mass, from the standpoint of imparting the cleansability.

The hair cleansing agent stock solution preferably contains a polyoxyethylene alkyl ether sulfate as the component (A1) from the standpoint of imparting the cleansability and the standpoint of the enhancement of the storage stability under a low temperature environment, the quality of foam immediately after discharging, the refoamability in cleansing the hair, the slippiness of foam, and the feeling of the hair after cleansing.

The content of the polyoxyethylene alkyl ether sulfate in the hair cleansing agent stock solution is preferably 5% by mass or more, more preferably 6% by mass or more, and further preferably 8% by mass or more, from the standpoint of imparting the cleansability and the standpoint of the enhancement of the storage stability under a low temperature environment, the quality of foam immediately after discharging, the refoamability in cleansing the hair, the slippiness of foam, and the feeling of the hair after cleansing, and is preferably 30% by mass or less, more preferably 20% by mass or less, and further preferably 15% by mass or less, from the standpoint of the enhancement of the storage stability. The specific range of the content of the polyoxyethylene alkyl ether sulfate in the hair cleansing agent stock solution is preferably 5 to 30% by mass, more preferably 6 to 20% by mass, and further preferably 8 to 15% by mass.

The content of the polyoxyethylene alkyl ether sulfate in the component (A1) is preferably 50% by mass or more, more preferably 70% by mass or more, further preferably 80% by mass of more, still further preferably 85% by mass or more, and still more further preferably 90% by mass or more, and may be 100% by mass, from the standpoint of imparting the cleansability and the standpoint of the enhancement of the storage stability under a low temperature environment, the quality of foam immediately after discharging, the refoamability in cleansing the hair, the slippiness of foam, and the feeling of the hair after cleansing.

The component (A) may contain one or more kind a surfactant selected from the group consisting of a cationic surfactant, a nonionic surfactant, and an amphoteric surfactant, in addition to the anionic surfactant (A1), for further imparting the target capability.

Nonionic Surfactant

Examples of the nonionic surfactant include a polyoxyalkylene alkyl ether, a polyoxyalkylene alkenyl ether, a polyoxyalkylene sorbitan fatty acid ester, a polyoxyalkylene fatty acid ester, an alkyl glucoside, an alkyl alkanolamide, an alkyl glyceryl ether, a higher fatty acid sucrose ester, a polyglycerin fatty acid ester, a polyoxyalkylene hydrogenated castor oil, and an alkylsaccharide, and one kind or two or more kinds thereof may be used.

In the nonionic surfactants exemplified above, the average addition molar number of ethylene oxide (which may be hereinafter referred to as an "EO average addition molar number") of the polyoxetylene alkyl ether, the polyoxetylene alkenyl ether, the polyoxetylene sorbitan fatty acid ester, the polyoxetylene fatty acid ester, and the polyoxetylene hydrogenated castor oil is preferably 2 or more, more preferably 3 or more, further preferably 5 or more, still further preferably 6 or more, and still more further preferably 8 or more, and is preferably 150 or less, more preferably 80 or less, further preferably 60 or less, and still further preferably 40 or less. The EO average addition molar number is preferably 2 or more and 150 or less, more preferably 3 or more and 80 or less, further preferably 5 or more and 60 or less, still further preferably 6 or more and 40 or less, and still more further preferably 8 or more and 40 or less. The EO average addition number is a number average value.

The alkyl group in the polyoxyalkylene alkyl ether, the alkyl glucoside, the alkyl alkanolamide, the alkyl glyceryl ether, and the alkylsaccharide, the alkenyl group in the polyoxyalkylene alkenyl ether, and the fatty acid in the polyoxyalkylene sorbitan fatty acid ester, polyoxyalkylene fatty acid ester, the higher fatty acid sucrose esters, and the polyglycerin fatty acid ester each preferably have 8 or more and 22 or less carbon atoms, more preferably 8 or more and 18 or less carbon atoms, and further preferably 10 or more and 18 or less carbon atoms.

Among the above, the nonionic surfactant is preferably one or more kind selected from the group consisting of a polyoxyalkylene alkyl ether, a polyoxyalkylene alkenyl ether, a polyoxyalkylene sorbitan fatty acid ester, a polyoxyalkylene fatty acid ester, an alkyl glucoside, an alkyl alkanolamide, an alkyl glyceryl ether, and a polyoxyalkylene hydrogenated castor oil, and more preferably one or more kind selected from the group consisting of a polyoxyalkylene alkyl ether, an alkyl glucoside, an alkyl alkanolamide, an alkyl glyceryl ether, and a polyoxyalkylene hydrogenated castor oil, from the standpoint of the use as a hair cleansing agent.

Cationic Surfactant

Examples of the cationic surfactant include (i) an alkyltrimethylammonium salt, (ii) an alkoxyalkyltrimethylammonium salt, (iii) a dialkyldimethylammonium salt, (iv) an alkylamidoalkyltrimethylammonium salt, (v) an alkyldimethylamine and a salt thereof, (vi) an alkoxyalkyldimethylamine and a salt thereof, and (vii) an alkylamidoalkyldimethylamine and a salt thereof, and one kind or two or more kinds thereof may be used.

The cationic surfactant preferably has a long-chain alkyl group having 8 or more and 22 or less carbon atoms, more preferably 8 or more and 18 or less carbon atoms, and further preferably 12 or more and 18 or less carbon atoms.

Examples of the salts of the amines (v) to (vii) include salts with an organic acid or an inorganic acid. Examples of the organic acid include an aliphatic monocarboxylic acid, such as acetic acid and a propionic acid; an aliphatic dicarboxylic acid, such as malonic acid, succinic acid, glutaric acid, adipic acid, maleic acid, and fumaric acid; an aromatic dicarboxylic acid, such as phthalic acid and isophthalic acid; a polycarboxylic acid, such as polyglutamic acid; a hydroxycarboxylic acid, such as glycolic acid, lactic acid, hydroxyacrylic acid, glyceric acid, malic acid, tartaric acid, and citric acid; and an acidic amino acid, such as glutamic acid and aspartic acid. Examples of the inorganic acid include hydrochloric acid, sulfuric acid, and phosphoric acid.

Amphoteric Surfactant

Examples of the amphoteric surfactant include a betaine type surfactant, an amine oxide type surfactant, and an amino acid type surfactant, and one kind or two or more kinds thereof may be used.

Examples of the betaine type surfactant include a carboxy betaine type, such as an alkyldimethylaminoacetic acid betaine and a fatty acid amidopropyl betaine; a sulfo betaine type, such as an alkylsulfo betaine and an alkylhydroxysulfo betaine; an imidazoline based betaine type; and a phospho betaine type.

The hydrocarbon group, such as the alkyl group and the alkenyl group, and the constitutional fatty acid of the amphoteric surfactant each preferably have 8 or more and 22 or less carbon atoms, more preferably 8 or more and 18 or less carbon atoms, and further preferably 12 or more and 18 or less carbon atoms.

The content of the component (A) in the hair cleansing agent stock solution is preferably 5% by mass or more, more preferably 6% by mass or more, and further preferably 8% by mass or more, from the standpoint of the dischargeability of foam through aerosol effect and the target capability as the hair cleansing agent, and is preferably 30% by mass or less, more preferably 20% by mass or less, and further preferably 15% by mass or less, from the standpoint of the enhancement of the storage stability. The specific range of the component (A) in the hair cleansing agent stock solution is preferably 5 to 30% by mass, more preferably 6 to 20% by mass, and further preferably 8 to 15% by mass.

Component (B): Nonionic Polymer

The hair cleansing agent stock solution constituting the hair cleansing agent of the present invention contains two or more kinds of nonionic polymers having weight average molecular weights different from each other as the component (B). The component (B) contained in the hair cleansing agent stock solution can enhance the storage stability under a low temperature environment, the quality of foam immediately after discharging, the refoamability in cleansing the hair, the slippiness of foam, and the feeling of the hair after cleansing, in combination with the effect of the propellant as the component (C).

The nonionic polymer used as the component (B) is preferably a water soluble polymer from the standpoint of the solubility in the hair cleansing agent stock solution.

It suffices that the nonionic polymers used as the component (B) are two or more kinds and have weight average molecular weights different from each other. The difference between the nonionic polymer having the largest weight average molecular weight and the nonionic polymer having the smallest weight average molecular weight in the component (B) is preferably 300,000 or more, more preferably 500,000 or more, further preferably 800,000 or more, still further preferably 1,000,000 or more, and still more further preferably 1,500,000 or more, from the standpoint of the enhancement of the storage stability under a low temperature environment, the quality of foam immediately after discharging, the refoamability in cleansing the hair, the slippiness of foam, and the feeling of the hair after cleansing, and is preferably 4,000,000 or less, more preferably 3,000,000 or less, and further preferably 2,000,000 or less, from the standpoint of the availability of the nonionic polymers. The specific range of the difference between the nonionic polymer having the largest weight average molecular weight and the nonionic polymer having the smallest weight average molecular weight in the component (B) is preferably 300,000 to 4,000,000, more preferably 500,000 to 4,000,000, further preferably 800,000 to 3,000,000, still further preferably 1,000,000 to 3,000,000, still more further preferably 1,500,000 to 3,000,000, and still more further preferably 1,500,000 to 2,000,000.

The weight average molecular weight of the component (B) can be measured, for example, by gel permeation chromatography (GPC) under the following condition.

Mobile phase: 50 mM LiBr, (1% $CH_3COOH$/ethanol)/(water)=3/7 (w/w)

Columns: TSKgel α-M (two columns in series) (produced by Tosoh Corporation)

Standard substance: polyethylene glycol

Examples of the nonionic polymer used as the component (B) include a water soluble polysaccharide, such as starch, cellulose, guar gum, tara gum, locust bean gum, and glucomannan; a hydroxyalkylated water soluble polysaccharide, such as hydroxyethyl cellulose and hydroxypropyl cellulose; a polyalkylene glycol compound, such as a polyethylene glycol and a polyethylene glycol-polypropylene glycol copolymer; and a polyvinyl alcohol, and one kind or two or more kinds thereof may be used.

Among the above, the nonionic polymer is preferably one or more kind selected form the group consisting of a water soluble polysaccharide, a hydroxyalkylated water soluble polysaccharide, and a polyalkylene glycol compound, more preferably one or more kind selected form the group consisting of starch, cellulose, guar gum, tara gum, locust bean gum, glucomannan, hydroxyethyl cellulose, hydroxypropyl cellulose, a polyethylene glycol, and a polyethylene glycol-polypropylene glycol copolymer, and further preferably one or more kind selected form the group consisting of hydroxyethyl cellulose, hydroxypropyl cellulose, a polyethylene glycol, and a polyethylene glycol-polypropylene glycol copolymer, from the standpoint of the enhancement of the storage stability under a low temperature environment, the quality of foam immediately after discharging, the refoamability in cleansing the hair, the slippiness of foam, and the feeling of the hair after cleansing.

The component (B) more preferably contains one or more kind selected form the group consisting of a polyethylene glycol and a polyethylene glycol-polypropylene glycol copolymer, and is further preferably a polyethylene glycol and a polyethylene glycol-polypropylene glycol copolymer, from the standpoint of the enhancement of the storage stability under a low temperature environment, the quality of foam immediately after discharging, the refoamability in cleansing the hair, the slippiness of foam, and the feeling of the hair after cleansing.

More specifically, the component (B) preferably contains a nonionic polymer (B1) having a weight average molecular weight of 1,000,000 or more and a nonionic polymer (B2) having a weight average molecular weight of 200,000 or less, from the standpoint of the enhancement of the storage stability under a low temperature environment, the quality of foam immediately after discharging, the refoamability in cleansing the hair, the slippiness of foam, and the feeling of the hair after cleansing.

The weight average molecular weight of the component (B1) is 1,000,000 or more, preferably 1,200,000 or more, and further preferably 1,500,000 or more, from the standpoint of the enhancement of the refoamability in cleansing the hair and the slippiness of foam, and is preferably 5,000,000 or less, more preferably 4,000,000 or less, and further preferably 3,500,000 or less, from the standpoint of the enhancement of the quality of foam immediately after discharging, the storage stability under a low temperature environment, and the feeling of the hair after cleansing, and the standpoint of the solubility in the hair cleansing agent stock solution. The specific range of the weight average molecular weight of the component (B1) is 1,000,000 or more, preferably 1,000,000 to 5,000,000, more preferably 1,000,000 to 4,000,000, further preferably 1,200,000 to 4,000,000, and still further preferably 1,500,000 to 3,500,000.

Two or more kinds of the nonionic polymers each having a weight average molecular weight of 1,000,000 or more may be used as the component (B1). In the case where two or more kinds of the component (B1) are used, it suffices that the weight average molecular weights of the nonionic polymers used each are 1,000,000 or more. In the case where two or more kinds of the component (B1) are used, the polymers may be the same kind polymer or may be different kind polymers.

The weight average molecular weight of the component (B2) is 200,000 or less, preferably 150,000 or less, and more preferably 120,000 or less, from the standpoint of the enhancement of the quality of foam immediately after discharging, the storage stability under a low temperature environment, and the feeling of the hair after cleansing, and is preferably 10,000 or more, more preferably 30,000 or more, and further preferably 50,000 or more, from the standpoint of the enhancement of the refoamability in cleansing the hair and the slippiness of foam. The specific range of the weight average molecular weight of the component (B2) is 200,000 or less, preferably 10,000 to 200,000, more preferably 30,000 to 150,000, and further preferably 50,000 to 120,000.

Two or more kinds of the nonionic polymers each having a weight average molecular weight of 200,000 or less may be used as the component (B2). In the case where two or more kinds of the component (B2) are used, it suffices that the weight average molecular weights of the nonionic polymers used each are 200,000 or less. In the case where two or more kinds of the component (B2) are used, the polymers may be the same kind polymer or may be different kind polymers.

The component (B1) and the component (B2) may be the same kind polymer or may be different kind polymers. The component (B1) and the component (B2) are preferably different kind polymers from the standpoint of the enhancement of the storage stability under a low temperature environment, the quality of foam immediately after discharging, the refoamability in cleansing the hair, the slippiness of foam, and the feeling of the hair after cleansing.

The component (B1) and the component (B2) each are preferably one or more kind selected from the group consisting of a polyethylene glycol and a polyethylene glycol-polypropylene glycol copolymer, and it is more preferred that the component (B1) is a polyethylene glycol, and the component (B2) is a polyethylene glycol-polypropylene glycol copolymer, from the standpoint of the enhancement of the storage stability under a low temperature environment, the quality of foam immediately after discharging, the refoamability in cleansing the hair, the slippiness of foam, and the feeling of the hair after cleansing.

The fact that the hair cleansing agent stock solution contains two or more kinds of nonionic polymers as the component (B), and the weight average molecular weights, the kinds, and the contents of the polymers can be determined, for example, in such a manner that the hair cleansing agent stock solution is fractionated by GPC under the aforementioned condition, and the resulting specimens each are analyzed.

In the case where the component (B) contains the component (B1) and the component (B2), the mass ratio [(B2)/(B1)] of the component (B2) with respect to the component (B1) in the hair cleansing agent stock solution is preferably 0.2 or more, more preferably 0.5 or more, further preferably 1.0 or more, still further preferably 2.0 or more, still more further preferably 3.0 or more, and still more further preferably 3.5 or more, and is preferably 30 or less, more preferably 20 or less, further preferably 15 or less, and still further preferably 12 or less, from the standpoint of the enhancement of the storage stability under a low temperature environment and the feeling of the hair after cleansing. The specific range of the mass ratio [(B2)/(B1)] of the component (B2) with respect to the component (B1) in the hair cleansing agent stock solution is preferably 0.2 to 30, more preferably 0.5 to 20, further preferably 1.0 to 20, still further preferably 1.0 to 15, still more further preferably 2.0 to 15, still more further preferably 3.0 to 15, and still more further preferably 3.5 to 12.

The content of the component (B) in the hair cleansing agent stock solution is preferably 0.01% by mass or more, more preferably 0.05% by mass or more, and further preferably 0.1% by mass or more, from the standpoint of the enhancement of the storage stability under a low temperature environment, the quality of foam immediately after discharging, the refoamability in cleansing the hair, the slippiness of foam, and the feeling of the hair after cleansing, and is preferably 5.0% by mass or less, more preferably 2.0% by mass or less, further preferably 1.0% by mass or less, and still further preferably 0.5% by mass or less, from the standpoint of regulating the hair cleansing agent stock solution to have a suitable viscosity and the standpoint of the enhancement of the storage stability. The specific range of the content of the component (B) in the hair cleansing agent stock solution is preferably 0.01 to 5.0% by mass, more preferably 0.05 to 2.0% by mass, and further preferably 0.05 to 1.0% by mass, and still further preferably 0.1 to 0.5% by mass.

The mass ratio [(B)/(A)] of the component (B) with respect to the component (A) in the hair cleansing agent stock solution is preferably 0.005 or more, more preferably 0.008 or more, and further preferably 0.01 or more, from the standpoint of the enhancement of the storage stability under a low temperature environment, the quality of foam immediately after discharging, the refoamability in cleansing the hair, the slippiness of foam, and the feeling of the hair after cleansing, and is preferably 0.1 or less, more preferably 0.05 or less, further preferably 0.03 or less, and still further preferably 0.015 or less, from the standpoint of regulating the hair cleansing agent stock solution to have a suitable viscosity and the standpoint of the enhancement of the storage stability. The specific range of the mass ratio [(B)/(A)] of the component (B) with respect to the component (A) in the hair cleansing agent stock solution is preferably 0.005 to 0.1, more preferably 0.008 to 0.05, further preferably 0.008 to 0.03, and still further preferably 0.01 to 0.015.

The total content of the component (A) and the component (B) in the hair cleansing agent stock solution is preferably 5.01% by mass or more, more preferably 5.1% by mass or more, further preferably 5.5% by mass or more, still further preferably 6.0% by mass or more, still more further preferably 6.5% by mass or more and still more further preferably 8.5% by mass or more, from the standpoint of the enhancement of the storage stability under a low temperature environment, the quality of foam immediately after discharging, the refoamability in cleansing the hair, the slippiness of foam, and the feeling of the hair after cleansing, and is preferably 40% by mass or less, more preferably 30% by mass or less, further preferably 20% by mass or less, and still further preferably 18% by mass or less, from the standpoint of the dischargeability of foam. The specific range of the total content of the component (A) and the component (B) in the hair cleansing agent stock solution is preferably 5.01 to 40% by mass, more preferably 5.1 to 30% by mass, further preferably 5.5 to 20% by mass, still further preferably 6.0 to 20% by mass, still more further preferably 6.5 to 18% by mass, and still more further preferably 8.5 to 18% by mass.

Aqueous Medium

The hair cleansing agent stock solution generally contains an aqueous medium from the standpoint of dissolving or dispersing the component (A), the component (B), and the other additional components. Examples of the aqueous medium include water and an organic solvent. Examples of the organic solvent include a lower alcohol, such as ethanol and isopropyl alcohol; and a low molecular weight diol or triol having 6 or less carbon atoms, such as 1,3-butylene glycol, glycerin, ethylene glycol, propylene glycol, and dipropylene glycol. Among these, water is preferred as the aqueous medium.

The content of the aqueous medium in the hair cleansing agent stock solution is preferably 60% by mass or more, and more preferably 70% by mass or more, and is preferably 98% by mass or less, and more preferably 94% by mass or less, from the standpoint of dissolving or dispersing the component (A), the component (B), and the other additional components, and the standpoint of the enhancement of the dischargeability of foam and the quality of foam immediately after discharging.

Additional Components

The hair cleansing agent stock solution may appropriately contain additional components in such a range that does not impair the object of the present invention. Examples of the components include components that have been generally mixed in hair cleansing agent, for example, a polymer other than the component (B), an organic acid or a salt thereof, an antioxidant, an oil, an antidandruff agent, a vitamin agent, an antimicrobial agent, an anti-inflammatory agent, an antiseptic agent, a chelating agent, a moisturizing agent, a pearlescent agent, a ceramide compound, a perfume, an ultraviolet ray absorbent, and a pH modifier. Among these, the hair cleansing agent stock solution preferably further contains an organic acid or a salt thereof and a perfume from the standpoint of imparting the target capability.

Examples of the organic acid include a carboxylic acid based compound and a sulfonic acid based compound, and one kind or two or more kinds thereof may be used.

Examples of the carboxylic acid based compound include an aliphatic monocarboxylic acid, such as acetic acid and propionic acid; an aromatic monocarboxylic acid, such as benzoic acid; an aliphatic dicarboxylic acid, such as malonic acid, succinic acid, glutaric acid, adipic acid, maleic acid, and fumaric acid; an aromatic dicarboxylic acid, such as phthalic acid and isophthalic acid; a polycarboxylic acid, such as polyglutamic acid; a hydroxycarboxylic acid, such as glycolic acid, lactic acid, hydroxyacrylic acid, glyceric acid, malic acid, tartaric acid, and citric acid; and an acidic amino acid, such as glutamic acid and asparaginic acid.

Examples of the sulfonic acid based compound include an aliphatic sulfonic acid, such as methanesulfonic acid and ethanesulfonic acid; and an aromatic sulfonic acid, such as p-toluenesulfonic acid.

The salt in the organic acid salt is preferably an alkali metal salt, more preferably one kind selected from the group consisting of a sodium salt and a potassium salt, and further preferably a sodium salt, from the standpoint of the use as a hair cleansing agent and the standpoint of the availability.

Among the above, the organic acid or a salt thereof is preferably one or more kind selected from the group consisting of an aliphatic dicarboxylic acid, a hydroxycarboxylic acid, an aromatic sulfonic acid, and salts thereof, and more preferably one or more kind selected from the group consisting of an aliphatic dicarboxylic acid, a hydroxycarboxylic acid, an aromatic sulfonic acid, from the standpoint of the enhancement of the storage stability under a low temperature environment, the quality of foam immediately after discharging, the refoamability in cleansing the hair, the slippiness of foam, and the feeling of the hair after cleansing.

The aliphatic dicarboxylic acid is more preferably succinic acid, and the hydroxycarboxylic acid is preferably one or more kind selected from the group consisting of lactic acid, malic acid, tartaric acid, and citric acid, and is more preferably malic acid. The aromatic sulfonic acid is preferably p-toluenesulfonic acid.

The content of the organic acid in the hair cleansing agent stock solution is preferably 0.1% by mass or more, more preferably 0.2% by mass or more, and further preferably 0.3% by mass or more, from the standpoint of the enhancement of the storage stability under a low temperature environment, the quality of foam immediately after discharging, the refoamability in cleansing the hair, the slippiness of foam, and the feeling of the hair after cleansing, and is preferably 20% by mass or less, more preferably 15% by mass or less, further preferably 10% by mass or less, and still further preferably 5.0% by mass or less, from the standpoint of the solubility in the hair cleansing agent stock solution. The specific range of the content of the organic acid in the hair cleansing agent stock solution is preferably 0.1 to 20% by mass, more preferably 0.2 to 15% by mass, further preferably 0.3 to 10% by mass, and still further preferably 0.3 to 5.0% by mass.

In the case where an organic acid salt is used, the amount of the organic acid salt in the hair cleansing agent stock solution converted to the corresponding organic acid is preferably within the aforementioned ranges.

The production method of the hair cleansing agent stock solution is not particularly limited, and the cosmetic hair preparation stock solution can be produced by blending and mixing the component (A), the component (B), and the other additional components used depending on necessity, by an ordinary method.

Component (C): Propellant

The propellant (C) constituting the hair cleansing agent of the present invention contains carbon dioxide. The component (C) that contains carbon dioxide enables discharge of fine dense foam, and simultaneously can enhance the refoamability in cleansing the hair through the functional mechanism described above.

The content of carbon dioxide in the propellant (C) is preferably 50% by mass or more, more preferably 70% by mass or more, further preferably 80% by mass or more, still further preferably 90% by mass or more, and still more further preferably 100% by mass, from the standpoint of the enhancement of the quality of foam immediately after discharging and the enhancement of the refoamability in cleansing the hair. Accordingly, it is preferred that the propellant (C) is formed only of carbon dioxide.

The component (C) may contain a liquified gas, such as nitrogen, propane, n-butane, isobutane, a liquefied petroleum gas (LPG) as a mixture of these compounds, dimethyl ether, and isopentane, as a propellant other than carbon dioxide, in such a range that does not impair the effects of the present invention.

The charge amount of the propellant (C) in the aerosol type hair cleansing agent of the present invention assuming that the total amount of the hair cleansing agent stock solution and the propellant (C) is 100% by mass is preferably 0.5% by mass or more, and more preferably 1% by mass or more, and is preferably 5% by mass or less, and more preferably 3% by mass or less, from the standpoint of the enhancement of the quality of foam immediately after discharging, the standpoint of the enhancement of the refoamability in cleansing the hair, and the standpoint of the achievement of the suitable discharge velocity. The specific range of the charge amount of the propellant (C) assuming that the total amount of the hair cleansing agent stock solution and the propellant (C) is 100% by mass is preferably 0.5 to 5% by mass, and more preferably 1 to 3% by mass.

The inner pressure of the aerosol container after charging the propellant (C) at 25° C. is regulated preferably to 0.1 MPa or more, and more preferably to 0.3 MPa or more, and is regulated preferably to 1.3 MPa or less, and more preferably to 1.0 MPa or less, for the achievement of a suitable discharge velocity. The specific range of the inner pressure of the aerosol container after charging the propellant (C) is preferably 0.1 to 1.3 MPa, and more preferably 0.3 to 1.0 MPa.

Aerosol Container

The aerosol type hair cleansing agent of the present invention is used after charging in an aerosol container. Examples of the aerosol container used include a known pressure resistant container, such as a metal container and a resin container, and a double structure container including a pressure resistant container having an inner bag housed therein. In the double structure container, it is preferred that the hair cleansing agent stock solution is housed in the inner bag, and the propellant (C) is charged between the pressure resistant container and the inner bag.

The preparation method of the aerosol type hair cleansing agent of the present invention is not particularly limited. For example, the aerosol type hair cleansing agent can be prepared in such a manner that the hair cleansing agent stock solution is charged in the pressure resistant container constituting the aerosol container, followed by attaching a valve thereto, and then the propellant (C) is charged through the valve.

Use Method of Aerosol Type Hair Cleansing Agent

The use method of the aerosol type hair cleansing agent of the present invention is not particularly limited, as far as the method includes steps of discharging the hair cleansing agent in the form of foam type from an aerosol container, and cleansing the hair by applying thereto.

Examples of the use method include a method including steps of coating the hair cleansing agent discharged in the form of foam type to the hair, and cleansing the hair. The step of cleansing the hair may include an operation of foaming the hair cleansing agent on the hair and then an operation of rinsing out the hair cleansing agent.

In relation to the aforementioned embodiments, the present invention further discloses the following embodiments.

<1>

An aerosol type hair cleansing agent containing a hair cleansing agent stock solution containing a surfactant (A) containing an anionic surfactant (A1) and two or more kinds of nonionic polymers (B) having weight average molecular weights different from each other, and a propellant (C) containing carbon dioxide.

<2>

The aerosol type hair cleansing agent according to the item <1>, wherein the component (A1) is one or more kind selected from the group consisting of an alkylbenzene sulfonate salt, an alkyl or alkenyl ether sulfate salt, an alkyl or alkenyl sulfate salt, an alkyl sulfonate salt, a saturated or unsaturated fatty acid salt, an alkyl or alkenyl ether carboxylate salt, an α-sulfo fatty acid salt, an N-acylamino acid salt, a phosphoric acid mono- or diester salt, and a sulfosuccinic acid ester salt, preferably one or more kind selected from the group consisting of an alkyl sulfate salt, an alkyl ether sulfate salt, an alkyl ether carboxylate salt, and an N-acylamino acid salt, more preferably one or more kind selected from the group consisting of an alkyl ether sulfate salt and an N-acylamino acid salt, and further preferably one or more kind selected from the group consisting of sodium laureth sulfate, ammonium laureth sulfate, and sodium cocoyl glutamate.

<3>

The aerosol type hair cleansing agent according to the item <2>, wherein the hydrocarbon group, such as the alkyl group and the alkenyl group, and the constitutional fatty acid of the component (A1) preferably has 8 or more and 22 or less carbon atoms, more preferably 8 or more and 18 or less carbon atoms, and further preferably 10 or more and 18 or less carbon atoms.

<4>

The aerosol type hair cleansing agent according to any one of the items <1> to <3>, wherein the content of the component (A1) in the component (A) is preferably 50% by mass or more, more preferably 70% by mass or more, further preferably 80% by mass or more, and still further preferably 90% by mass or more.

<5>

The aerosol type hair cleansing agent according to any one of the items <1> to <4>, wherein the hair cleansing agent stock solution contains a polyoxyethylene alkyl ether sulfate as the component (A1) in an amount of 5% by mass or more, preferably 5 to 30% by mass, more preferably 6 to 20% by mass, and further preferably 8 to 15% by mass.

<6>

The aerosol type hair cleansing agent according to the item <5>, wherein the content of the polyoxyethylene alkyl ether sulfate in the component (A1) is preferably 50% by mass or more, more preferably 70% by mass or more, further preferably 80% by mass of more, still further preferably 85% by mass or more, and still more further preferably 90% by mass or more.

<7>

The aerosol type hair cleansing agent according to any one of the items <1> to <6>, wherein the content of the component (A) in the hair cleansing agent stock solution is preferably 5 to 30% by mass, more preferably 6 to 20% by mass, and further preferably 8 to 15% by mass.

<8>

The aerosol type hair cleansing agent according to any one of the items <1> to <7>, wherein the difference between the nonionic polymer having the largest weight average molecular weight and the nonionic polymer having the smallest weight average molecular weight in the component (B) is preferably 300,000 to 4,000,000, more preferably 500,000 to 4,000,000, further preferably 800,000 to 3,000,000, still further preferably 1,000,000 to 3,000,000, still more further preferably 1,500,000 to 3,000,000, and still more further preferably 1,500,000 to 2,000,000.

<9>

The aerosol type hair cleansing agent according to any one of the items <1> to <8>, wherein the component (B) is one or more kind selected from the group consisting of a water soluble polysaccharide, a hydroxyalkylated water soluble polysaccharide, a polyalkylene glycol compound, and a polyvinyl alcohol, preferably one or more kind selected from the group consisting of a water soluble polysaccharide, a hydroxyalkylated water soluble polysaccharide, and a polyalkylene glycol compound, more preferably one or more kind selected form the group consisting of starch, cellulose, guar gum, tara gum, locust bean gum, glucomannan, hydroxyethyl cellulose, hydroxypropyl cellulose, a polyethylene glycol, and a polyethylene glycol-polypropylene glycol copolymer, further preferably one or more kind selected form the group consisting of hydroxyethyl cellulose, hydroxypropyl cellulose, a polyethylene glycol, and a polyethylene glycol-polypropylene glycol copolymer, still further preferably contains one or more kind selected form the group consisting of a polyethylene glycol and a polyethylene glycol-polypropylene glycol copolymer, and is further preferably a polyethylene glycol and a polyethylene glycol-polypropylene glycol copolymer.

<10>

The aerosol type hair cleansing agent according to any one of the items <1> to <9>, wherein the component (B) contains a nonionic polymer (B1) having a weight average molecular weight of 1,000,000 or more and a nonionic polymer (B2) having a weight average molecular weight of 200,000 or less, and the component (B1) and the component (B2) are preferably different kind polymers.

<11>

The aerosol type hair cleansing agent according to the item <10>, wherein the weight average molecular weight of the component (B1) is preferably 1,000,000 to 5,000,000, more preferably 1,000,000 to 4,000,000, further preferably 1,200,000 to 4,000,000, and still further preferably 1,500,000 to 3,500,000.

<12>

The aerosol type hair cleansing agent according to the item <10> or <11>, wherein the weight average molecular weight of the component (B2) is preferably 10,000 to 200,000, more preferably 30,000 to 150,000, and further preferably 50,000 to 120,000.

<13>

The aerosol type hair cleansing agent according to any one of the items <10> to <12>, wherein the component (B1) and the component (B2) each are one or more kind selected from the group consisting of a polyethylene glycol and a polyethylene glycol-polypropylene glycol copolymer.

<14>

The aerosol type hair cleansing agent according to the item <13>, wherein the component (B1) is a polyethylene glycol.

<15>

The aerosol type hair cleansing agent according to the item <13> or <14>, wherein the component (B2) is a polyethylene glycol-polypropylene glycol copolymer.

<16>

The aerosol type hair cleansing agent according to any one of the items <10> to <15>, wherein the mass ratio [(B2)/(B1)] of the component (B2) with respect to the component (B1) in the hair cleansing agent stock solution is preferably 0.2 to 30, more preferably 0.5 to 20, further preferably 1.0 to 20, still further preferably 1.0 to 15, still more further preferably 2.0 to 15, still more further preferably 3.0 to 15, and still more further preferably 3.5 to 12.

<17>

The aerosol type hair cleansing agent according to any one of the items <1> to <16>, wherein the content of the component (B) in the hair cleansing agent stock solution is preferably 0.01 to 5.0% by mass, more preferably 0.05 to 2.0% by mass, and further preferably 0.05 to 1.0% by mass, and still further preferably 0.1 to 0.5% by mass.

<18>

The aerosol type hair cleansing agent according to any one of the items <1> to <17>, wherein the mass ratio [(B)/(A)] of the component (B) with respect to the component (A) in the hair cleansing agent stock solution is preferably 0.005 to 0.1, more preferably 0.008 to 0.05, further preferably 0.008 to 0.03, and still further preferably 0.01 to 0.015.

<19>

The aerosol type hair cleansing agent according to any one of the items <1> to <18>, wherein the total content of the component (A) and the component (B) in the hair cleansing agent stock solution is preferably 5.01 to 40% by mass, more preferably 5.1 to 30% by mass, further preferably 5.5 to 20% by mass, still further preferably 6.0 to 20% by mass, still more further preferably 6.5 to 18% by mass, and still more further preferably 8.5 to 18% by mass.

<20>

The aerosol type hair cleansing agent according to any one of the items <1> to <19>, wherein the hair cleansing agent stock solution contains an aqueous medium in an amount of preferably 60% by mass or more, and more preferably 70% by mass or more, and in an amount of preferably 98% by mass or less, and more preferably 94% by mass or less.

<21>

The aerosol type hair cleansing agent according to any one of the items <1> to <20>, wherein the aqueous medium is one or more kind selected from the group consisting of water, a lower alcohol, and a low molecular weight diol or triol having 6 or less carbon atoms, preferably one or more kind selected from the group consisting of water, ethanol, isopropyl alcohol, 1,3-butylene glycol, glycerin, ethylene glycol, propylene glycol, and dipropylene glycol, and more preferably water.

<22>

The aerosol type hair cleansing agent according to any one of the items <1> to <21>, wherein the hair cleansing agent stock solution further contains an organic acid or a salt thereof and a perfume.

<23>

The aerosol type hair cleansing agent according to the item <22>, wherein the content of the organic acid in the hair cleansing agent stock solution is preferably 0.1 to 20% by mass, more preferably 0.2 to 15% by mass, further preferably 0.3 to 10% by mass, and still further preferably 0.3 to 5.0% by mass.

<24>

The aerosol type hair cleansing agent according to any one of the items <1> to <23>, wherein the content of carbon dioxide in the propellant (C) is preferably 50% by mass or more, more preferably 70% by mass or more, further preferably 80% by mass or more, still further preferably 90% by mass or more, and still more further preferably 100% by mass.

<25>

The aerosol type hair cleansing agent according to any one of the items <1> to <24>, wherein the charge amount of the propellant (C) in the aerosol type hair cleansing agent assuming that the total amount of the hair cleansing agent stock solution and the propellant (C) is 100% by mass is preferably 0.5 to 5% by mass, and more preferably 1 to 3% by mass.

<26>

An aerosol type hair cleansing agent containing a hair cleansing agent stock solution containing a surfactant (A) containing an anionic surfactant (A1) and two or more kinds of nonionic polymers (B) having weight average molecular weights different from each other, and a propellant (C) containing carbon dioxide, the component (A1) being one or more kind selected from the group consisting of sodium laureth sulfate, ammonium laureth sulfate, and sodium cocoyl glutamate, the component (B) containing a nonionic polymer (B1) having a weight average molecular weight of 1,000,000 or more and a nonionic polymer (B2) having a weight average molecular weight of 200,000 or less, the component (B1) and the component (B2) each being one or more kind selected from the group consisting of a polyethylene glycol and a polyethylene glycol-polypropylene glycol copolymer, the content of the component (A) in the hair cleansing agent stock solution being 5 to 30% by mass, the mass ratio [(B)/(A)] of the component (B) with respect to the component (A) in the hair cleansing agent stock solution being 0.005 to 0.1.

<27>

A method for using the aerosol type hair cleansing agent according to any one of the items <1> to <26>, including steps of discharging the hair cleansing agent in the form of foam type from an aerosol container, and applying to the hair.

EXAMPLES

The present invention will be described with reference to examples below, but the present invention is not limited to the range of the examples.

Examples 1 to 8 and Comparative Examples 1 to 18

Production and Evaluation of Aerosol Type Hair Cleansing Agents

The components to be blended in the hair cleansing agent stock solution were blended according to each of the compositions shown in Tables 1 to 3, and then mixed until uniform, so as to prepare a hair cleansing agent stock solution. Subsequently, 50 g of the hair cleansing agent stock solution and the propellant shown in the tables were charged to make the mass ratio shown in the tables in an aerosol container having a capacity of 100 mL (container type: BL35A115-H, produced by Toyo Seikan Kaisha, Ltd., inner coating: epoxy phenol type, outer surface: silver solid color (or white)), so as to produce an aerosol type hair cleansing agent. The inner pressure of the aerosol container after charging the propellant was regulated to a range of 0.65 to 0.85 MPa.

The aerosol type hair cleansing agents thus produced were evaluated in the following manner. The results are shown in Tables 1 to 3.

The blended amounts shown in the tables each were the active ingredient amount (% by mass).

Storage Stability at Low Temperature

The aerosol type hair cleansing agents of the examples each obtained by charging the hair cleansing agent stock solution and the propellant in the aerosol container each were allowed to stand still in depositories at 5° C. and −5° C. for 28 days, and the appearance of the contents of the aerosol container was visually observed and evaluated by the following two criteria.

Evaluation Standard

A: Transparent and uniform in both 5° C. storage and −5° C. storage

B: White turbidity, deposition, separation, or precipitation observed in at least one of 5° C. storage and −5° C. storage

Foaming (Quality of Foam Immediately after Discharging)

For each of the aerosol type hair cleansing agents of the examples, approximately 0.5 g of the hair cleansing agent was discharged in the form of foam type from the aerosol container to the palm. After sufficiently moistening a hair tress having a length of 30 cm, a width of 6 cm, and a weight of 20 g with warm water at 35 to 40° C., the discharged hair cleansing agent was placed thereon and foamed 10 times, at which the state of foam was evaluated by the following three criteria.

Evaluation Standard

A: Foam containing fine bubbles having uniform size

B: Foam containing small amount of bubbles having various sizes

C: Foam containing large amount of bubbles having various sizes

Slippiness of Foam

For each of the aerosol type hair cleansing agents of the examples, approximately 0.5 g of the hair cleansing agent was discharged in the form of foam type from the aerosol container to the palm. After sufficiently moistening a hair tress having a length of 30 cm, a width of 6 cm, and a weight of 20 g with warm water at 35 to 40° C., the discharged hair cleansing agent was placed thereon and foamed 10 times, at which the slippiness in combing the hair tress with fingers was evaluated by the following three criteria.

Evaluation Standard

A: Combing smoothly with fingers with no resistance of hair

B: Combing smoothly with fingers, but slight resistance of hair observed

C: Resistance of hair observed, and fingers caught in combing

Refoamability

For each of the aerosol type hair cleansing agents of the examples, approximately 0.5 g of the hair cleansing agent was discharged in the form of foam type from the aerosol container to the palm. After sufficiently moistening a hair tress having a length of 30 cm, a width of 6 cm, and a weight of 20 g with warm water at 35 to 40° C., the discharged hair cleansing agent was placed thereon and foamed 10 times, and then further foamed 10 times, at which the state of foaming was evaluated by the following three criteria.

Evaluation Standard

A: Foam increased on hair tress

B: No change of foam on hair tress

C: Foam worn out and decreased

Smoothness of Hair after Cleansing

For each of the aerosol type hair cleansing agents of the examples, approximately 0.5 g of the hair cleansing agent was discharged in the form of foam type from the aerosol container to the palm. After sufficiently moistening a hair tress having a length of 30 cm, a width of 6 cm, and a weight of 20 g with warm water at 35 to 40° C., the discharged hair cleansing agent was placed thereon and foamed 20 times, and then rinsed out with warm water at 35 to 40° C. for 10 seconds, followed by drying with towel, at which the feeling of the hair was evaluated by the following three criteria.

Evaluation Standard

A: Fingers pass through without feeling rough or stiff in the hair, without getting caught B: Fingers pass through the hair without getting caught, but you can feel a slight roughness and stiffness in the hair C: Feeling rough and rough hair, causing snags when fingering

TABLE 1

| | | | Example | | | | | | | |
|---|---|---|---|---|---|---|---|---|---|---|
| | | | 1 | 2 | 3 | 4 | 5 | 6 | 7 | 8 |
| Composition of hair cleansing agent stock solution (% by mass) | (A) | (A-1) Na laureth sulfate | 10.77 | 10.77 | 10.77 | 10.77 | 10.77 | 10.77 | 7.54 | 5.39 |
| | | (A1-2) Ammonium laureth sulfate | 1.00 | 1.00 | 1.00 | 1.00 | 1.00 | 1.00 | 0.70 | 0.50 |
| | | (A1-3) Na cocoyl glutamate | 0.97 | 0.97 | 0.97 | 0.97 | 0.97 | 0.97 | 0.68 | 0.49 |
| | (B) | (B1-1) PEG-45M (M.W. 2,000,000) | 0.1 | 0.02 | 0.01 | 0.02 | 0.03 | 0.05 | 0.03 | 0.03 |
| | | (B1-2) PEG/PPG-2000/200 copolymer (M.W. 3,000,000) | | | | | | | | |
| | | (B1-3) Hydroxyethyl cellulose (M.W. 1,500,000) | | | | | | | | |
| | | (B') Xanthan gum (M.W. 2,000,000) | | | | | | | | |
| | | (B2-1) PEG/PPG-2000/200 copolymer (M.W. 100,000) | 0.1 | 0.1 | 0.15 | 0.15 | 0.15 | 0.15 | 0.15 | 0.15 |
| | | Organic acid | 2.5 | 2.5 | 2.5 | 2.5 | 2.5 | 2.5 | 2.5 | 2.5 |
| | | Perfume | 0.3 | 0.3 | 0.3 | 0.3 | 0.3 | 0.3 | 0.3 | 0.3 |
| | | Solvent | 1.05 | 1.05 | 1.05 | 1.05 | 1.05 | 1.05 | 1.05 | 1.05 |
| | | Water | balance | | | | | | | |
| | | Total | 100.0 | 100.0 | 100.0 | 100.0 | 100.0 | 100.0 | 100.0 | 100.0 |
| | | Content of component (A) (% by mass) | 12.74 | 12.74 | 12.74 | 12.74 | 12.74 | 12.74 | 8.92 | 6.38 |
| | | Content of component (B) (% by mass) | 0.20 | 0.12 | 0.16 | 0.17 | 0.18 | 0.20 | 0.18 | 0.18 |
| | | Content of components (A) + (B) (% by mass) | 12.94 | 12.86 | 12.90 | 12.91 | 12.92 | 12.94 | 9.10 | 6.56 |
| | | Mass ratio (B)/(A) | 0.016 | 0.009 | 0.013 | 0.013 | 0.014 | 0.016 | 0.020 | 0.028 |
| | | Mass ratio (B2)/(B1) | 1 | 5 | 15 | 7.5 | 5 | 3 | 5 | 5 |
| | | Content of polyoxyethylene alkyl sulfate in hair cleansing agent stock solution (% by mass) | 11.77 | 11.77 | 11.77 | 11.77 | 11.77 | 11.77 | 8.24 | 5.89 |
| | | Content of polyoxyethylene alkyl sulfate in component (A1) (% by mass) | 92.4 | 92.4 | 92.4 | 92.4 | 92.4 | 92.4 | 92.4 | 92.3 |
| Composition of hair cleansing agent (% by mass) | | Hair cleansing agent stock solution | 97.8 | 97.8 | 97.8 | 97.8 | 97.8 | 97.8 | 97.8 | 97.8 |
| | (C) | Carbon dioxide | 2.2 | 2.2 | 2.2 | 2.2 | 2.2 | 2.2 | 2.2 | 2.2 |
| | | LPG | | | | | | | | |
| Evaluation result | | Storage stability at low temperature | A | A | A | A | A | A | A | A |
| | | Foaming (quality of foam immediately after discharging) | B | B | A | A | A | A | A | B |
| | | Slippiness of foam | A | A | B | A | A | A | B | B |
| | | Refoamability | A | A | A | A | A | A | A | B |
| | | Smoothness of hair after cleansing | B | A | A | A | A | B | B | B |

TABLE 2

| | | | Comparative Example | | | | | | | | | | |
|---|---|---|---|---|---|---|---|---|---|---|---|---|---|
| | | | 1 | 2 | 3 | 4 | 5 | 6 | 7 | 8 | 9 | 10 | 11 |
| Composition of hair cleansing agent stock solution (% by mass) | (A) | (A-1) Na laureth sulfate | 10.77 | 10.77 | 10.77 | 10.77 | 10.77 | 10.77 | 10.77 | 10.77 | 10.77 | 10.77 | 10.77 |
| | | (A1-2) Ammonium laureth sulfate | 1.00 | 1.00 | 1.00 | 1.00 | 1.00 | 1.00 | 1.00 | 1.00 | 1.00 | 1.00 | 1.00 |
| | | (A1-3) Na cocoyl glutamate | 0.97 | 0.97 | 0.97 | 0.97 | 0.97 | 0.97 | 0.97 | 0.97 | 0.97 | 0.97 | 0.97 |
| | (B) | (B1-1) PEG-45M (M.W. 2,000,000) | 0.03 | | | | | | | | | | |
| | | (B1-2) PEG/PPG-2000/200 copolymer (M.W. 3,000,000) | | | | | | | 0.02 | 0.03 | 0.06 | 0.1 | 0.2 |
| | | (B1-3) Hydroxyethyl cellulose (M.W. 1,500,000) | | | | | | | | | | | |
| | | (B') Xanthan gum (M.W. 2,000,000) | | | | | | | | | | | |
| | | (B2-1) PEG/PPG-2000/200 copolymer (M.W. 100,000) | 0.15 | 0.1 | 0.15 | 0.2 | 0.3 | 0.5 | | | | | |
| | | Organic acid | 2.5 | 2.5 | 2.5 | 2.5 | 2.5 | 2.5 | 2.5 | 2.5 | 2.5 | 2.5 | 2.5 |
| | | Perfume | 0.3 | 0.3 | 0.3 | 0.3 | 0.3 | 0.3 | 0.3 | 0.3 | 0.3 | 0.3 | 0.3 |
| | | Solvent | 1.05 | 1.05 | 1.05 | 1.05 | 1.05 | 1.05 | 1.05 | 1.05 | 1.05 | 1.05 | 1.05 |
| | | Water | balance | | | | | | | | | | |
| | | Total | 100.0 | 100.0 | 100.0 | 100.0 | 100.0 | 100.0 | 100.0 | 100.0 | 100.0 | 100.0 | 100.0 |
| | | Content of component (A) (% by mass) | 12.74 | 12.74 | 12.74 | 12.74 | 12.74 | 12.74 | 12.74 | 12.74 | 12.74 | 12.74 | 12.74 |

TABLE 2-continued

| | | | Comparative Example | | | | | | | | | | |
|---|---|---|---|---|---|---|---|---|---|---|---|---|---|
| | | | 1 | 2 | 3 | 4 | 5 | 6 | 7 | 8 | 9 | 10 | 11 |
| | | Content of component (B) (% by mass) | 0.18 | 0.10 | 0.15 | 0.20 | 0.30 | 0.50 | 0.02 | 0.03 | 0.06 | 0.10 | 0.20 |
| | | Content of components (A) + (B) (% by mass) | 12.92 | 12.84 | 12.89 | 12.94 | 13.04 | 13.24 | 12.76 | 12.77 | 12.80 | 12.84 | 12.94 |
| | | Mass ratio (B)/(A) | 0.014 | 0.008 | 0.012 | 0.016 | 0.024 | 0.039 | 0.002 | 0.002 | 0.005 | 0.008 | 0.016 |
| | | Mass ratio (B2)/(B1) | 5 | — | — | — | — | — | 0 | 0 | 0 | 0 | 0 |
| | | Content of polyoxyethylene alkyl sulfate in hair cleansing agent stock solution (% by mass) | 11.77 | 11.77 | 11.77 | 11.77 | 11.77 | 11.77 | 11.77 | 11.77 | 11.77 | 11.77 | 11.77 |
| | | Content of polyoxyethylene alkyl sulfate in component (A1) (% by mass) | 92.4 | 92.4 | 92.4 | 92.4 | 92.4 | 92.4 | 92.4 | 92.4 | 92.4 | 92.4 | 92.4 |
| Composition of hair cleansing agent (% by mass) | | Hair cleansing agent stock solution | 88.0 | 97.8 | 97.8 | 97.8 | 97.8 | 97.8 | 97.8 | 97.8 | 97.8 | 97.8 | 97.8 |
| | (C) | Carbon dioxide | | 2.2 | 2.2 | 2.2 | 2.2 | 2.2 | 2.2 | 2.2 | 2.2 | 2.2 | 2.2 |
| | | LPG | 12 | | | | | | | | | | |
| Evaluation result | | Storage stability at low temperature | A | A | A | A | A | A | B | B | B | B | B |
| | | Foaming (quality of foam immediately after discharging) | B | B | A | A | A | A | A | A | A | A | A |
| | | Slippiness of foam | C | C | C | C | C | C | A | A | A | A | A |
| | | Refoamability | C | B | B | B | B | B | A | A | A | A | A |
| | | Smoothness of hair after cleansing | A | A | A | A | B | B | A | A | B | B | B |

TABLE 3

| | | | Comparative Example | | | | | | |
|---|---|---|---|---|---|---|---|---|---|
| | | | 12 | 13 | 14 | 15 | 16 | 17 | 18 |
| Composition of hair cleansing agent stock solution (% by mass) | (A) | (A-1) Na laureth sulfate | 10.77 | 10.77 | 10.77 | 10.77 | 10.77 | 10.77 | 10.77 |
| | | (A1-2) Ammonium laureth sulfate | 1.00 | 1.00 | 1.00 | 1.00 | 1.00 | 1.00 | 1.00 |
| | | (A1-3) Na cocoyl glutamate | 0.97 | 0.97 | 0.97 | 0.97 | 0.97 | 0.97 | 0.97 |
| | (B) | (B1-1) PEG-45M (M.W. 2,000,000) | 0.03 | 0.05 | 0.1 | 0.2 | | | |
| | | (B1-2) PEG/PPG-2000/200 copolymer (M.W. 3,000,000) | | | | | | | |
| | | (B1-3) Hydroxyethyl cellulose (M.W. 1,500,000) | | | | | 0.3 | 1 | |
| | | (B') Xanthan gum (M.W. 2,000,000) | | | | | | | 0.2 |
| | | (B2-1) PEG/PPG-2000/200 copolymer (M.W. 100,000) | | | | | | | |
| | | Organic acid | 2.5 | 2.5 | 2.5 | 2.5 | 2.5 | 2.5 | 2.5 |
| | | Perfume | 0.3 | 0.3 | 0.3 | 0.3 | 0.3 | 0.3 | 0.3 |
| | | Solvent | 1.05 | 1.05 | 1.05 | 1.05 | 1.05 | 1.05 | 1.05 |
| | | Water | balance | | | | | | |
| | | Total | 100.0 | 100.0 | 100.0 | 100.0 | 100.0 | 100.0 | 100.0 |
| | | Content of component (A) (% by mass) | 12.74 | 12.74 | 12.74 | 12.74 | 12.74 | 12.74 | 12.74 |
| | | Content of component (B) (% by mass) | 0.03 | 0.05 | 0.10 | 0.20 | 0.30 | 1.00 | 0.20 |
| | | Content of components (A) + (B) (% by mass) | 12.77 | 12.79 | 12.84 | 12.94 | 13.04 | 13.74 | 12.94 |
| | | Mass ratio (B)/(A) | 0.002 | 0.004 | 0.008 | 0.016 | 0.024 | 0.078 | 0.016 |
| | | Mass ratio (B2)/(B1) | 0 | 0 | 0 | 0 | 0 | 0 | 0 |
| | | Content of polyoxyethylene alkyl sulfate in hair cleansing agent stock solution (% by mass) | 11.77 | 11.77 | 11.77 | 11.77 | 11.77 | 11.77 | 11.77 |
| | | Content of polyoxyethylene alkyl sulfate in component (A1) (% by mass) | 92.4 | 92.4 | 92.4 | 92.4 | 92.4 | 92.4 | 92.4 |
| Composition of hair cleansing agent (% by mass) | | Hair cleansing agent stock solution | 97.8 | 97.8 | 97.8 | 97.8 | 97.8 | 97.8 | 97.8 |
| | (C) | Carbon dioxide | 2.2 | 2.2 | 2.2 | 2.2 | 2.2 | 2.2 | 2.2 |
| | | LPG | | | | | | | |
| Evaluation result | | Storage stability at low temperature | A | A | A | A | A | A | B |
| | | Foaming (quality of foam immediately after discharging) | C | C | C | C | C | C | C |

TABLE 3-continued

| | Comparative Example | | | | | | |
|---|---|---|---|---|---|---|---|
| | 12 | 13 | 14 | 15 | 16 | 17 | 18 |
| Slippiness of foam | A | A | A | A | C | C | A |
| Refoamability | A | A | B | B | A | A | A |
| Smoothness of hair after cleansing | A | B | C | C | C | C | B |

The components used in the tables were as follows.

Surfactant (A)

(A1-1) Na laureth sulfate: Sodium polyoxyethylene (2) lauryl ether sulfate, "Emal 227", produced by Kao Corporation, active ingredient: 27% by mass (A1-2) Ammonium laureth sulfate: ammonium polyoxyethylene (1) alkyl(C10-16) ether sulfate, "Emal 125A", produced by Kao Corporation, active ingredient: 25% by mass (A1-3) Na cocoyl glutamate: "Amisoft CS-22B", produced by Ajinomoto Healthy Supply Co., Inc., active ingredient: 25% by mass Polymer (B1-1) PEG-45M: polyethylene glycol, weight average molecular weight: 2,000,000, "Polyox WSR N-60K", produced by Dow Chemical Company (B1-2) PEG/PPG-2000/200 copolymer: polyethylene glycol-polypropylene glycol copolymer, weight average molecular weight: 3,000,000, "Alkox E100", produced by Meisei Chemical Works, Ltd.

(B1-3) Hydroxyethyl cellulose: weight average molecular weight: 1,500,000, "HEC Daicel SE850K", produced by Daicel Finechem, Ltd.

(B') Xanthan gum: weight average molecular weight: 2,000,000, "Echo Gum", produced by DSP Gokyo Food & Chemical Co., Ltd.

(B2-1) PEG/PPG-2000/200 copolymer: polyethylene glycol-polypropylene glycol copolymer, weight average molecular weight: 100,000, "Alkox EP1010N", produced by Meisei Chemical Works, Ltd.

As shown in Table 1, it is understood that the aerosol type hair cleansing agents of the examples are excellent in all the storage stability under a low temperature environment, the quality of foam immediately after discharging, the slippiness of foam in cleansing, the refoamability, and the smoothness of the hair after cleansing.

On the other hand, as shown in Tables 2 and 3, the aerosol type hair cleansing agent of Comparative Example 1 containing no carbon dioxide as the propellant and the aerosol type hair cleansing agents of Comparative Examples 2 to 6 containing only one kind of the nonionic polymer having a weight average molecular weight of 200,000 or less as the polymer are inferior in the slippiness of foam in cleansing. The aerosol type hair cleansing agents of Comparative Examples 7 to 17 containing only one kind of the nonionic polymer having a weight average molecular weight of 1,000,000 or more as the polymer and the aerosol type hair cleansing agent of Comparative Example 18 containing only one kind of an anionic polymer (B') having a weight average molecular weight of 1,000,000 or more as the polymer are inferior in any of the storage stability under a low temperature environment, the quality of foam immediately after discharging, the slippiness of foam in cleansing, and the smoothness of the hair after cleansing.

INDUSTRIAL APPLICABILITY

According to the present invention, an aerosol type hair cleansing agent that is excellent in storage stability under a low temperature environment and the quality of foam immediately after discharging, and is also good in refoamability in cleansing the hair, slippiness of foam, and good feeling of the hair after cleansing can be provided.

The invention claimed is:

1. An aerosol hair cleansing agent comprising a hair cleansing agent stock solution comprising:
- 6 to 20 mass % of a surfactant (A) containing an anionic surfactant (A1), and
- 0.1 to 0.5 mass % of two or more nonionic polymers (B) having weight average molecular weights different from each other, and
- a propellant (C) containing carbon dioxide,
- wherein the component (B) contains a polyethylene glycol (B1) having a weight average molecular weight of 1,500,0000 or more and 3,500,000 or less and contains a polyethylene glycol-polypropylene glycol copolymer (B2) having a weight average molecular weight of 50,000 or more and 120,000 or less,
- wherein the ratio of (B2) to (B1) is 3.0 to 15, and
- wherein (A1) is one or more members selected from the group consisting of sodium laureth sulfate, ammonium laureth sulfate, and sodium cocoyl glutamate.

2. The aerosol hair cleansing agent according to claim 1, wherein the hair cleansing agent stock solution has a content of the component (A) of 8% by mass or more and 15% by mass or less.

3. The aerosol hair cleansing agent according to claim 1, wherein the hair cleansing agent stock solution has a mass ratio of the component (B) with respect to the component (A) of 0.005 or more and 0.1 or less.

4. The aerosol hair cleansing agent according to claim 1, wherein a mass ratio of the component (B) with respect to the component (A) in the hair cleansing agent stock solution is 0.01 or more and 0.015 or less.

5. The aerosol hair cleansing agent according to claim 1, wherein a total content of the component (A) and the component (B) in the hair cleansing agent stock solution is 8.5% by mass or more and 18% by mass or less.

6. A method of applying to hair the aerosol hair cleansing agent according to claim 1, comprising discharging a foam of the aerosol hair cleansing agent from an aerosol container, and applying to the hair.

7. The method of claim 6, wherein the hair cleansing agent stock solution has a content of the component (A) of 8% by mass or more and 15% by mass or less.

8. The method of claim 6, wherein the hair cleansing agent stock solution has a mass ratio of the component (B) with respect to the component (A) of 0.005 or more and 0.1 or less.

9. The method of claim 6, wherein a mass ratio of the component (B) with respect to the component (A) in the hair cleansing agent stock solution is 0.01 or more and 0.015 or less.

10. The method of claim 6, wherein a total content of the component (A) and the component (B) in the hair cleansing agent stock solution is 8.5% by mass or more and 18% by mass or less.

* * * * *